United States Patent
Brand

[11] Patent Number: 5,432,344
[45] Date of Patent: Jul. 11, 1995

[54] APPLIANCE FOR THE OXIDATION OF COMPONENTS IN ORGANIC SAMPLES, AND PROCESS THEREFOR

[75] Inventor: Willi Brand, Stuhr, Germany

[73] Assignee: Finnigan Mat GmbH, Bremen, Germany

[21] Appl. No.: 114,776

[22] Filed: Aug. 31, 1993

[30] Foreign Application Priority Data

Sep. 26, 1992 [DE] Germany .................. 42 32 301.0

[51] Int. Cl.$^6$ ............................................. H01J 49/04
[52] U.S. Cl. ..................................................... 250/288
[58] Field of Search ............................ 250/288, 288 A

[56] References Cited

U.S. PATENT DOCUMENTS

| | | | |
|---|---|---|---|
| 4,843,980 | 7/1989 | Markham et al. | 110/342 |
| 5,012,052 | 4/1991 | Hayes | 250/288 |

FOREIGN PATENT DOCUMENTS

| | | |
|---|---|---|
| 0306332 | 3/1989 | European Pat. Off. |
| 0306333 | 3/1989 | European Pat. Off. |
| 0419167 | 3/1991 | European Pat. Off. |

OTHER PUBLICATIONS

AA Accession No. 47-11-J-00069 (1984).
Matthews et al., Analytical Chemistry, vol. 50, No. 11, Sep. 1978, pp. 1465–1473.
Gylhyon, Laboratory Practice, vol. 37, No. 10, 1988, pp. 93–95, 97.
Chemical Abstracts, vol. 110, 1989, Ref. 73954p.
Chemical Abstracts, vol. 81, 1974, Ref. 119,583e.
Chemical Abstracts, vol. 80, 1974, Ref. 30978.
Hayes et al., Organic Geochemistry, vol. 16, No. 4–6, 1990, pp. 1115–1128.

*Primary Examiner*—Jack I. Berman
*Attorney, Agent, or Firm*—Flehr, Hohbach, Test, Albritton & Herbert

[57] ABSTRACT

The invention relates to an appliance for the oxidation of components in organic samples, in particular for the oxidation of components emerging from a gas chromatograph and for preparation for an analysis of isotope ratios by mass spectrometry, having a chamber with a gas inlet and a gas outlet, having an oxidizer inside the chamber and, in particular, having a heating appliance for the chamber. It is known to use copper oxide as oxidizer. The latter requires continual reoxidation to achieve sufficiently good results of measurement. In addition, at high temperatures, coagulation of the copper occurs. An oxidizer composed of nickel oxide is provided according to the present invention. This is extremely stable to temperature. The chamber receiving the oxidizer is advantageously lined with $Al_2O_3$.

8 Claims, 2 Drawing Sheets

APPLIANCE FOR THE OXIDATION OF COMPONENTS IN ORGANIC SAMPLES, AND PROCESS THEREFOR

BACKGROUND OF THE INVENTION

The invention relates to an appliance for the oxidation of components in organic samples, in particular for the oxidation of components emerging from a gas chromatograph and for preparation for an analysis of isotope ratios by mass spectrometry, having a chamber with a gas inlet and a gas outlet, having an oxidizer inside the chamber and, in particular, having a heating appliance for the chamber, characterized in that the oxidizer is nickel oxide. The invention furthermore relates to a process for isotope ratio analysis.

One of the many possible uses of investigations by mass spectrometry is the analysis of isotope ratios. Thus, the analysis of carbon and nitrogen isotopes in components in organic samples is of interest. It is known for the investigation of gaseous components to arrange a gas chromatograph upstream of the mass spectrometer and to separate the individual components in time. It is furthermore known to oxidize the components before carrying out the analysis by mass spectrometry. In this case, for example the carbon in the organic sample is converted into $CO_2$ and the hydrogen into $H_2O$. $CO_3$ results as the product of oxidation of various components. This means that the analysis can be carried out on the basis of a single compound ($CO_2$). Furthermore, it is relatively simple to manipulate $CO_2$ because it can be introduced at room temperature in the form of a gas without heated lines into the ion source of the mass spectrometer. The oxidation of the organic components takes place in a combustion oven (combusion interface). In this the organic components are heated and oxidized with the aid of a special oxidizer. This process is known in the literature as IRM-GCMS (isotope ratio monitoring gas chromatography/mass spectrometry) or GC-IRMS (gas chromatography isotope ratio mass spectrometry). The oxidizer regarded as particularly advantageous to date has been copper oxide (CuO). Corresponding analytical processes and relevant apparatus are described in Analytical Chemistry, Vol. 50, No. 11, September 1978, pages 1465–1473 and Org. Geochem. Vol. 16, Nos. 4–6, 1990, pages 1115–1128. The oxidizer is, as a rule, provided with a supplementary platinum catalyst.

The use of copper oxide as oxidizer has various disadvantages. A high temperature is necessary for the oxidation of the organic components, for example a temperature near 1000° C. for methane. At this temperature the copper oxide is decomposed to Cu and $O_2$. This means that the oxidation of the organic components is incomplete. To avoid this effect it is necessary for the copper to be continually reoxidized. Appropriate additional appliances must be provided. In addition, at such high temperatures there is even coagulation of the copper, which thus substantially loses its oxidizing ability. Despite these disadvantages, to date copper oxide (CuO) has been regarded as the most suitable oxidizer.

OBJECT AND SUMMARY OF INVENTION

It is an object of the present invention to provide an appliance and a process which makes it possible to oxidize organic components even at high temperatures or in fact provides good results irrespective of the temperature.

The object is achieved according to the invention by providing nickel oxide (NiO) as oxidizer. Experiments have revealed that nickel oxide makes isotope ratio analyses possible substantially irrespective of the temperature. In view of the predominant position of copper oxide on its own in the literature and in practice, this is a surprising finding.

It is advantageous for the chamber to have inside the appliance—the oven tube—a lining or coating of $Al_2O_3$, or it is made of $Al_2O_3$. This avoids reaction of the oxidizer, nickel oxide, with the material of the chamber, for example the chamber walls.

In accordance with the appliance described above, the process according to the invention also operates with nickel oxide as oxidizer.

DETAILED DESCRIPTION OF PREFERRED EMBODIMENT

In connection with the following explanations, express reference is made to the state of the art mentioned in the introduction to the description and to the appliances and processes described therein. The present exemplary embodiments represent modifications of the appliances and processes shown therein.

Figure 1:
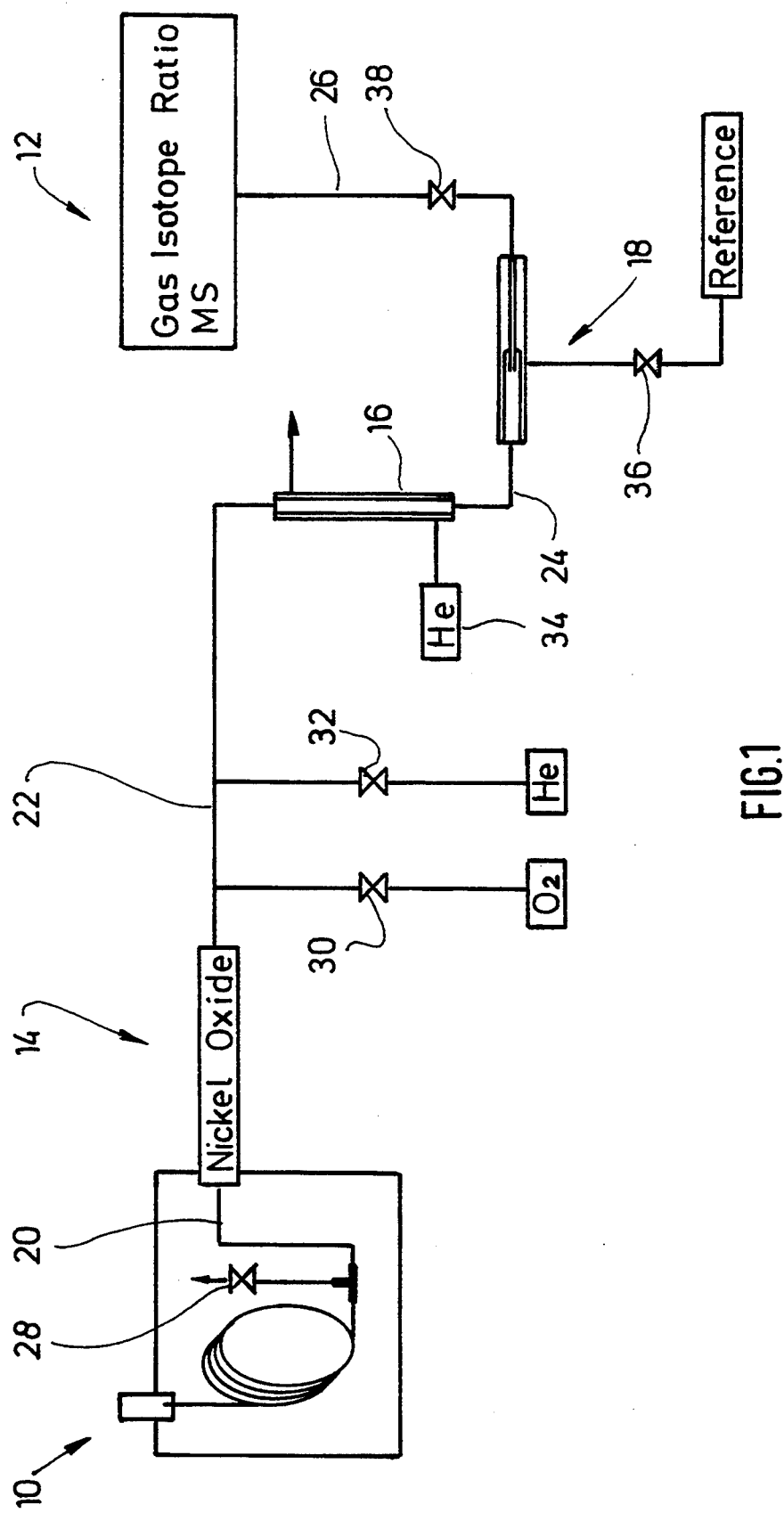
FIG. 1 a diagrammatic representation of a system for isotope ratio analysis.

FIG. 1 shows in diagrammatic representation a system for isotope ratio analysis having a gas chromatograph 10, having a mass spectrometer 12 (MS) and having a combustion oven (combustion interface) 14 located between them. The latter is described in detail in conjunction with FIG. 2.

Located between the combustion oven 14 and the mass spectrometer 12 is a water separator 16, and between the latter and the mass spectrometer 12 is a capillary 18 to restrict the inflow of gas into the ion source (Open Split Interface).

The described components are each connected via line sections 20, 22, 24 and 26. A branch with a discharge valve 28 is located in line section 20, that is to say downstream of the gas chromatograph 10. An oxygen feed with a valve 30 and a helium feed via a valve 32 are provided in the line section 22 downstream of the combustion oven 14. Another helium line 34 is located at the transition from the water separator 16 into line section 24.

A reference sample with a known isotope ratio can be introduced through a valve 36 in the region of the inlet capillary 18. Finally, line section 26 can be closed off from the mass spectrometer 12 by a valve 38.

An organic sample is separated into components in the gas chromatograph 10. These components emerge consecutively from the gas chromatograph through line 20. The components undergo oxidation in the combustion oven 14. During this the carbon which is present is oxidized to carbon dioxide. Water ($H_2O$) is formed from hydrogen. The oxidation takes place inside the combustion oven 14 at high temperature, for example at 800° to 1140° C. for methane. The oxidizer provided in the combustion oven 14 is nickel oxide as wire or as fine mesh.

The water which is produced is separated from the carbon dioxide in the water separator 16. Used as water separator is a hygroscopic membrane whose outside is flushed with dry helium. Other processes, for example, cryogenic or chemical, are also possible.

The carbon dioxide is fed, alternating with a reference gas, through the capillary 18 to the mass spectrometer 12. A multiple collector is provided in the latter and has a fixed setting to mass numbers 44 and 45, corresponding to the carbon isotopes $^{13}C$ and $^{12}C$. The $^{13}C/^{12}C$ isotope ratio can be measured continuously without changing the electrical setting of the mass spectrometer. In this case, changes in the intensity of the $CO_2$ signal have, to a first approximation, no effect on the measured $^{13}C/^{12}C$ isotope ratio because the ion fluxes belonging to masses 45 and 44 change simultaneously. The result is an extremely high accuracy of measurement of the isotope ratios.

The oxygen feed-in via the valve 30 is provided as oxygen source in the case of reoxidation of the nickel oxide. The reoxidation is necessary at considerably longer intervals than in the known process with copper oxide. The oxygen is passed in countercurrent through the combustion oven 14 and emerges through the valve 28. In a similar way, the valve 32 is provided for introducing a helium countercurrent. At the start of a measurement, initially the solvent flows out of the gas chromatograph 10. This is retained in the so-called backflush process. The exit for helium is likewise the valve 28. Finally, a helium feed-in 34 is provided at the downstream end of the water separator 16. The helium emerges again at the upstream end of the water separator 16, at the arrow 34a, and is used for the drying, which is necessary from time to time, of the water separator 16.

In place of the oxidation of carbon described above, analogous oxidation of other elements, for example of sulphur, is possible. Nitrogen may also be liberated in the combustion process. If isotope analysis of this nitrogen is required, the carbon dioxide, which interferes in this case, is retained in a cold trap, for example by cooling a short line section with liquid nitrogen.

Figure 2:
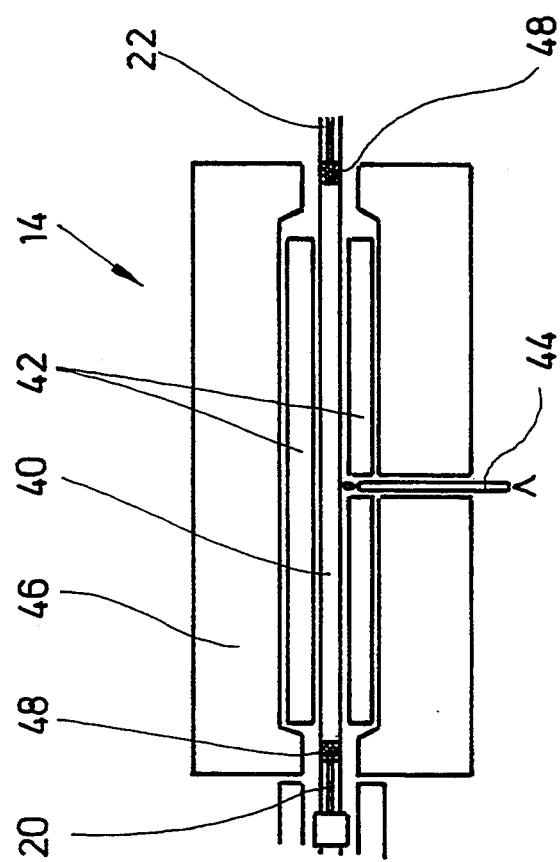
FIG. 2 a diagrammatic representation of a combustion oven for the oxidation of organic components.

FIG. 2 shows the construction of the combustion oven 14 in a detailed cross-sectional representation. An oven tube 40 is surrounded by heating elements 42. Approximately in the middle there is provided an aperture in the heating elements 42 for a thermal element 44 to determine the temperature of the oven tube 40. The latter has a diameter of about 0.6 mm or less. The elements described previously are jacketed all round with a thick-walled insulation 46.

The inside of the oven tube 40 is packed with nickel oxide, for example as wire or fine mesh. The oven tube 40 is coated on the inside with $Al_2O_3$ or is entirely composed of this material. The upstream and downstream lines 20, 22, 24 have a somewhat smaller internal diameter than the oven tube 40. Retaining plugs 48 made of a coarser $Al_2O_3$ material are located at the transitions of the oven tube 40 to each of the lines 20 and 22. For reasons of clarity, the oxygen feed with the valve 30, the helium feed with the valves 32 and 34, and the water separator 16 are not included in the drawing in FIG. 2.

In a preferred embodiment, the combustion oven 14 additionally contains copper oxide as oxidizer, in particular as mixture or aggregate with nickel oxide. The copper oxide does in fact release oxygen more quickly than nickel oxide. However, the oxygen does not simply emerge from the oven but brings about reoxidation of the used nickel oxide. Other additives or additional constituents, in particular having the described action, are also possible.

The combustion oven 14 preferably contains platinum as catalyst.

I claim:

1. Appliance for the oxidation of components in organic samples emerging from a gas chromatograph and for preparation for an analysis of isotope ratios by mass spectrometry, having a chamber (combustion oven 14) with a gas inlet and a gas outlet, having an oxidizer inside the chamber and having a heating appliance (heating elements 42) for the chamber, characterized in that the oxidizer is nickel oxide.

2. Appliance according to claim 1, characterized in that copper oxide is provided in addition to nickel oxide as oxidizer.

3. Appliance according to claim 1 or 2, characterized in that the oxidizer contains platinum as catalyst.

4. Appliance according to one or more of claims 1 to 2, characterized in that the chamber (combustion oven 14) has an internal lining or coating of $Al_2O_3$ or is made of $Al_2O_3$.

5. Process for isotope ratio analysis of carbon and nitrogen wherein an organic sample is separated into components in a gas chromatograph (10), the components are exposed to a decomposition and oxidation process in a combustion oven (14), where appropriate unwanted by-products are fed to a mass spectrometer (12), characterized in that nickel oxide is used as oxidizer in the combustion oven (14).

6. Process according to claim 5, characterized in that copper oxide is used in addition to nickel oxide as oxidizer.

7. Process according to claim 5 or 6, characterized in that a catalyst is used, in particular platinum, in the combustion oven.

8. Process according to claim 5 where the temperatures in the combustion oven range between 800° to 1140° C.

* * * * *